United States Patent [19]

Devlin

[11] Patent Number: 4,851,432

[45] Date of Patent: Jul. 25, 1989

[54] THERAPEUTIC USES OF OLIGOMERS OF 15-DEHYDROPROSTAGLANDIN $B_1$ AND OLIGOMERS OF DERIVATIVES OF 15-DEHYDROPROSTAGLANDIN B1

[76] Inventor: Thomas M. Devlin, 183 Beaumont Rd., Devon, Pa. 19333

[21] Appl. No.: 52,812

[22] Filed: May 21, 1987

[51] Int. Cl.$^4$ ............................................. A61K 31/19
[52] U.S. Cl. ................................... 514/573; 514/530
[58] Field of Search ................................ 514/530, 573

[56] References Cited

U.S. PATENT DOCUMENTS 4,153,808  5/1979  Polis et al. ........................... 562/503
4,245,111  1/1981  Polis et al. ........................... 560/121

OTHER PUBLICATIONS

Polis et al., *Proc. Nat. Acad. Sci.*, 63, 229 (1969), "Regeneration of Oxidative Phosphorylation in Aged Mitochandria".

Polis et al., *Proc. Nat. Acad. Sci.*, 76, 1598, (1979), "Protection and Reactivation of Oxidative Phosphorylation in Mitochandria".

Serhan et al., *The Journal of Immunology*, 125, 2020, (1980), "$PGB_x$ a Prostaglandin Derivative Mimics th Action of the Calcium Larophone".

Ohnishi et al., *Biochemical and Biophysical Research Communications*, "Calcium Larophone Activity of a Prostaglandin $B_1$ Derivative $PGB_x$".

*Primary Examiner*—Mary C. Lee
*Assistant Examiner*—E. Brendan Magrab
*Attorney, Agent, or Firm*—Caesar, Rivise, Bernstein, Cohen & Pokotilow, Ltd.

[57] ABSTRACT

This invention relates to the therapeutic uses of oligomers of 15-dehydroprostaglandin $B_1$ and oligomers of 16, 16'-dimethyl-15-dehydro $PGB_1$ and oligomers or other 16 carbon substituted 15-dehydro $PGB_1$ compounds (hereinafter referred to as oligomers of $PGB_1$) in tissue ischemia, hyposix and anoxia, (hereinafter referred to collectively as tissue ischemia) and in protecting isolated organs (hearts, kidneys etc.) and cells (whole blood, erythrocytes, platelets, etc.) during in vitro transfer and storage; and as a pharmacological agent in abnormal conditions in humans and animals in which alteration in cellular calcium is a mediator in the disease process.

9 Claims, No Drawings

THERAPEUTIC USES OF OLIGOMERS OF 15-DEHYDROPROSTAGLANDIN B₁ AND OLIGOMERS OF DERIVATIVES OF 15-DEHYDROPROSTAGLANDIN B1

BACKGROUND OF THE INVENTION

This invention relates to the therapeutic uses of oligomers of 15-dehydroprostaglandin $B_1$ and oligomers of 16, 16'-dimethyl-15-dehydro $PGB_1$ and oligomers of other 16 carbon substituted 15-dehydro $PGB_1$ compounds (hereinafter referred to as oligomers of $PGB_1$) in tissue ischemia, hypoxia and anoxia, (hereinafter referred to collectively as tissue ischemia) and in protecting isolated organs (hearts, kidneys etc.) and cells (whole blood, erythrocytes, platelets, etc.) during in vitro transfer and storage; and as a pharmacological agent in abnormal conditions in humans and animals in which alteration in cellular calcium is a mediator in the disease process.

The derivatives of 15-dehydroprostaglandin $B_1$ described in this disclosure include oligomeric forms of the parent 15-dehydroprostaglandin $B_1$ and of the 16, 16'-dimethyl-15-dehydroprostaglandin, both series of which have been synthesized in co-pending application Ser. No. 769,045, filed Aug. 23, 1985 1985, inventor: George Nelson, the entire disclosure of which is incorporated herein by reference, and of other oligomeric forms from derivatives in which there has been a substitution on carbon 16 of the 15-dehydroprostaglandin. The specific oligomeric forms include the dimer, trimer, tetramer and pentamer and mixtures thereof. Henceforth, they will be referred to generically as oligo-$PGB_1$.

Prostaglandin ($PGB_x$), as set forth in Polis U.S. Pat. Nos. 4,153,808 and 4,245,111 has been determined to be useful for a wide variety of in vivo and in vitro adverse biological conditions, including the reversal of degenerative changes in mitochondria, the protection of the heart against cardiac insults, the protection and reversal of anoxic damage to the brain, and the improvement of mammalian performance for conditioned physiological tasks. Such prostaglandin ($PGB_x$) is prepared by the base catalyzed reaction of $PGB_1$ as set forth in Polis U.S. Pat. No. 4,153,808. An improved method for synthesizing and purifying $PGB_x$ which is defined in Polis U.S. Pat. No. 4,245,111 as a mixture of polymers of prostaglandin $B_1$, involves utilizing solutions of (1) 15-keto $PGB_1$ methyl ester in ethanol and (2) 2 N KOH solution.

However, $PGB_x$ as prepared by the method of both Polis patents, is a complex mixture. It was not possible to isolate the actual active components. Moreover, the Polis processes for syntheses of $PGB_x$ was very drastic and not specific, leading to a variety of compounds and degradation products. Quality control on the Polis processes was difficult and each batch of $PGB_x$ could vary significantly, reducing its value as a therapeutic agent. On the other hand, the defined oligo $PGB_1$'s of the present invention are known structures wherein the synthetic procedure, as set forth in the aforesaid Nelson pending patent application, can be monitored for impurities.

Moreover, the defined structures of the oligo $PGB_1$'s of the present invention also permit critical evaluation of the human and animal toxicity of the individual oligomers. The metabolic disposition of the drug can be evaluated because radiolabeled material can be prepared for preclinical drug evaluation with the assurance that the labeled material is the drug and not inactive contaminants as might occur in $PGB_x$.

The foregoing properties of the present invention are in sharp contrast to the products produced by the methods of the Polis patents. As previously stated, the Polis procedures were very drastic and the Polis products contained an unknown number of differing compounds of varying size, wherein the most active fraction had a mean molecular weight of 2200–2400. It has not been feasible to purify such materials or to determine the chemical structures of the various components. Although the mixture of $PGB_x$ of Polis has been evaluated as a protective agent in tissue ischemia with some success, the striking disadvantages of $PGB_x$ as set forth hereinabove, have rendered it generally unusable. It is improbable that the active components of $PGB_x$ will ever be isolated or identified, thus, making $PGB_x$ an unlikely candidate for development as a drug. The passage of approximately ten years has further confirmed the foregoing.

It is known that an ischemic condition occurs when the circulation to a tissue or organ is impaired. Such condition can be caused by a collapse of the circulation, a blockage of blood flow to the tissue by an embolism or clot of an artery supplying a tissue, or by a reduction in the blood volume or blood pressure such as occurs in shock. The condition leads to first a hypoxic (low oxygen) then to an anoxic (no oxygen) condition. Tissue without adequate blood supply cannot receive adequate nutrients or remove toxic waste products of metabolism.

A series of degenerative changes occur in the tissue subjected to ischemia which are initially reversible but with time become irreversible. The condition leads to an infarction in the tissue in which the cells die and the tissue becomes necrotic. All tissues are potentially subject to the problems of ischemia, but those conditions which are most life threatening are when ischemia occurs to the heart (myocardial infarct or heart attack), brain (stroke), kidney, spinal cord and lung.

Ischemic conditions of other tissues are also clinically significant, including the stomach, (gastric ulcers) and intestines (necrosis) and during surgery where the blood supply may be temporarily disrupted. The most important time for therapeutic intervention is the period immediately following the ischemic phase, when the tissue is attempting to adapt to the changed blood supply and reperfusion of the tissue by blood is occurring. If the tissue cannot survive the post-ischemic period, then cell and tissue death occurs.

Most tissues do not regenerate readily, thus the function of the organ can be compromised, and, depending on the organ, serious neurological and/or physical impairment and death of the tissue and individual can occur. At the cellular level, the loss of the blood supply deprives the cells of oxygen.

At the morphological level, there is a disorganization of cellular structures, a swelling of cell organelles particularly mitochondria, membrane disruption and lysis of cellular organelles. Of particular importance are the changes in mitochondria, which utilize oxygen to supply the cells with chemical energy. Swelling of mitochondria leads to a potentially irreversible damage of the chemical mechanism of energy production (oxidative phosphorylation).

A consequence of the foregoing loss is the inability of mitochondria to participate in the control of intracellular calcium levels. An increase in calcium triggers a number of potentially deleterious reactions, including stimulation of specific hydrolytic reactions involving arachadonic acid formation (phospholipase $A_2$). Arachadonic acid is the precursor for prostaglandins, prostacyclin, thromboxanes and leucotrienes; these metabolites have a variety of effects on cellular activities.

Very similar morphological and biochemical changes occur to many tissues and cells during storage in vitro. During the period between removal of an organ (e.g., heart, kidney, liver, etc.) from a donor and transplant into a recipient, the organ is subject to the same changes as observed in ischemia of organs in situ.

The changes observed in mitochondria in situ are also observed with mitochondria isolated from tissues. Freshly isolated mitochondria free of other cellular components have the characteristics of mitochondria in a tissue. When incubated in vitro in a reaction system for measuring their biochemical activities they maintain these in situ characteristics, but after 20–30 minutes they begin to swell and there is a loss of their ability to utilize oxygen, carry out oxidative phosphorylation, maintain their membrane potential, and maintain the intramitochondrial calcium. Isolated mitochondria can be employed to study the effectiveness of agents in protecting against tissue ischemia.

It will be seen that the present invention recognizes therapeutic uses of defined chemical compounds which would have a protective role on a tissue during ischemia and/or during the immediate post-ischemic period. Accordingly, the present invention provides for therapeutic uses of important pharmacological agents and reduces the risk of permanent disability and death. Such therapeutic uses of compounds are also valuable in storing of tissues during transplant and the storage in vitro of cells such as platelets or erythrocytes.

SUMMARY OF THE INVENTION

In accordance with the present invention, there is provided therapeutic uses of a series of structurally defined oligomers of 15-dehydro $PGB_1$, 16, 16'-dimethyl-15-dehydro $PGB_1$ and other 16 carbon substituted 15-dehydro $PGB_1$ compounds (hereinafter referred to as oligomers of $PGB_1$) as drugs for human and animals for protection against the damage caused by tissue ischemia, the use of these compounds as protective agents during transfer and storage in vitro of tissues and cells and as a pharmacological agent in abnormal conditions in humans and animals in which alteration in cellular calcium is a mediator in the disease process (hereinafter therapeutic agent affecting alteration in cellular calcium and leading to diseases attributable thereto).

Oligomeric derivatives of 15-dehydro $PGB_1$ and 16, 16'dimethyl-15-dehydro $PGB_1$ have been synthesized and characterized by Nelson as set forth in the aforesaid co-pending application. With the 15-dehydro $PGB_1$, a dimer is first formed with a chemical bond between carbon 10 of one molecule and either carbon 13' or 14' of another or carbon 16 of one molecule and carbon 13' or 14' of another; in the latter reaction, an additional bond may form between either carbons 14 and 14' or 13 and 14' of the respective monomers creating a new five member ring structure. The trimer, tetra and pentamer can be formed by sequential addition of another monomer to the dimer, etc.

With 16, 16'dimethyl-15-dehydro $PGB_1$ as the starting material, the chemical bond occurs only between carbons 10 of one molecule and either carbons 13' or 14' of the other; perferentially a bond between carbon 10 and carbon 13 of two molecules is formed because of steric hindrance. Subsequent oligomerizations occur between the dimer and a monomer with the preferred linkage between carbons 10 and 13 on respective molecules.

Some of the compounds of the present invention are shown as follows:

15-keto $PGB_1$ DIMER FORMATION

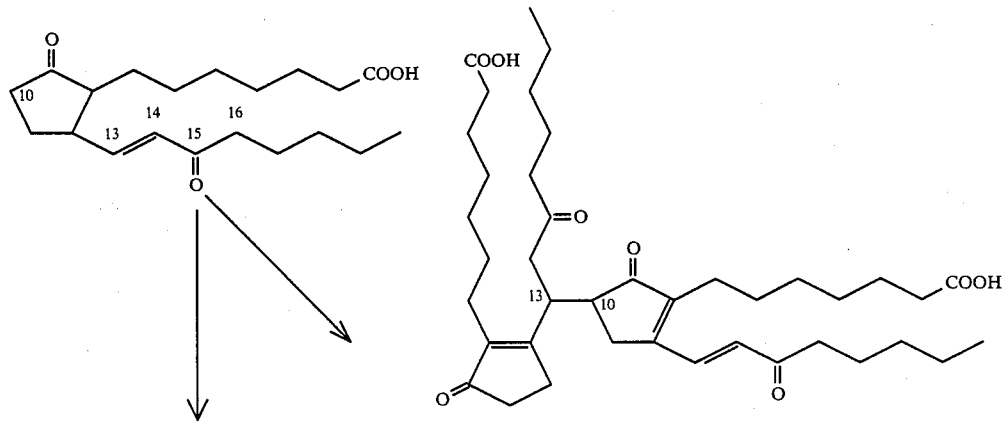

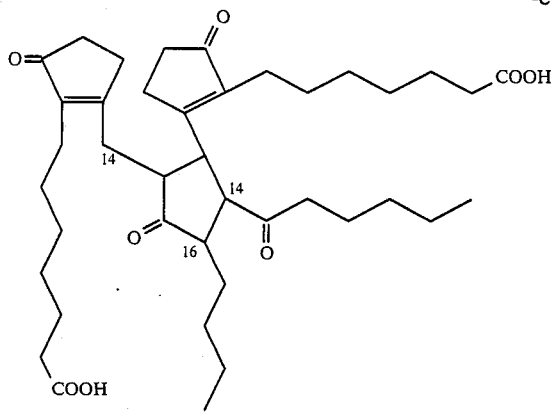

16,16' diMethyl-15-dehydro Prostaglandin B Trimer

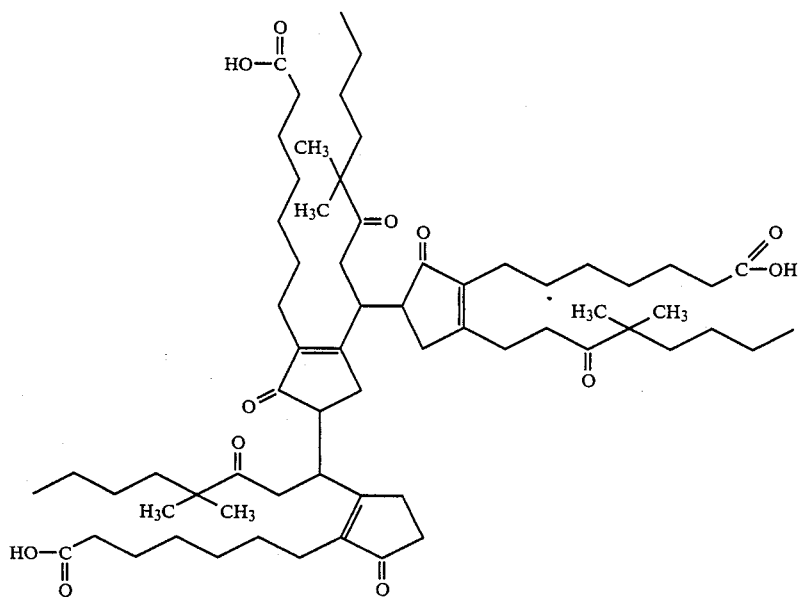

DESCRIPTION OF THE PREFERRED EMBODIMENT

The dimer, trimer and tetramer of both the 15-dehydro $PGB_1$ and 16, 16'dimethyl-15-dehydro $PGB_1$ series protect mitochondria isolated from rat liver from the loss of function during incubation in vitro and each has the ability to alter the calcium concentration of isolated mitochondria and to release calcium from isolated sarcoplasmic reticulum vesicles and intact dispersed liver cells. Thus, the oligo $PGB_1$'s should exert a protective effect in vivo on tissues subject to ischemia.

When isolated rat liver mitochondria are incubated in vitro in a system containing 0.018 M potassium phosphate, pH 7.4, 0.007 M $MgCl_2$, 0.060 M potassium chloride and 0.010 M glutamate or other substrate they maintain their ability to catalyze oxidative phosphorylation for about 20 to 30 minutes at which time the activity goes to zero. Simultaneously the mitochondria enlarge and there is a loss of intramitochondrial components (e.g. calcium, cytochrome c, dehydrogenases, etc.). Incubation with between 3 and 10 micro molar of the various oligo $PGB_1$'s of the present invention prevents the loss of activity and extends the period of viability two to three times of the control. In order of activity, the dimer is less active than the trimer and the trimer and tetramer have about the same level of activity. The monomer has no activity.

The oligomers of $PGB_1$ of the present invention have calcium ionphoretic activity (the ability to transport calcium across a membrane) with isolated cellular organelles (mitochondria and sarcoplasmic reticulum) and intact dispersed liver cells. The trimeric and tetrameric derivatives of both 15-dehydro $PGB_1$ and 16, 16'dimethyl-15-dehydro $PGB_1$ are most active and are effective in the range of 5 to 20 micro molar. The ionophoretic activity is unique in that it requires the presence of potassium or sodium and alters the binding of calcium in the organelle and cells. The results suggest that the oligomers of $PGB_1$ are altering the cellular membranes to control the calcium movements.

Isolated intact cells from rat liver suspended in sodium chloride 0.120 M, 0.008 M potassium chloride, 0.002 M potassium phosphate, 0.002 M magnesium sulfate, 0.001 M calcium chloride and 0.022 sodium bicarbonate maintain their viability after isolation for at least 8 hours in the presence of oxygen. When subjected to an oxygen free atmosphere (anoxia) the cells lose their ability to survive within one to two hours; this is measured either by the cells ability to exclude a dye or by the release of intracellular enzymes, such as lactic dehydrogenase. The oligomers of $PGB_1$ extend the survival of the liver cells two to three times of the control.

The $PGB_1$ oligomers can be administered intravenously or intramuscular injection. The preferred dosage will be between 1 mg and 5 mg per kilo of body weight of animal or human being. With animals intraperitoneal injection is also used.

A preferred injection is 1 mg per kilo active ingredient per kilo of body weight of animal or human being, given four times each day.

In the case of protecting organs and cells, the concentration of $PGB_1$ oligomer is preferably between 1 and 5 micromolar or 1 mg per kg of tissue active ingredient.

The dosage in those abnormal conditions in which the objective is to effectively control intracellular calcium is the same as treating ischemia. Such conditions are exemplified by shock.

Without further elaboration, the foregoing will so fully illustrate my invention that others may, by applying current or future knowledge, adopt the same for use under various conditions of service.

I claim:

1. A method for treating tissue ischemia in a warm blooded animal comprising administering to said animal a therapeutically effective amount of a $PGB_1$ oligomer selected from the group consisting of $PGB_1$-Dimer, $PGB_2$-Trimer, 16,16'-diMethyl-PGB Dimer and 16,16'-diMethyl-PGB Trimer.

2. The method of claim 1 involving administering an injection of 1 mg per kilo active ingredient, given four times each day.

3. A method for protecting isolated organs and cells during in vitro transfer and storage, said method comprising exposing said isolated organs and cells to a therapeutically effective amount of a $PGB_1$ oligomer.

4. The method of claim 3 wherein said PGB oligomer is maintained in solution at a concentration of between one and five micromolars.

5. A method for treatment of shock affecting alteration in cellular calcium in a warm blooded animal, said method comprising administering to said animal a therapeutically effective amount of a $PGB_1$ oligomer.

6. The method of claim 5 involving administering an injection of 1 mg per kilo active ingredient, given four times each day.

7. A method for treatment of shock or other conditions in a warm blooded animal in which control of cellular calcium is critical, said method comprising administering to said animal a therapeutically effective amount of a $PGB_1$ oligomer.

8. The method of claim 7 involving administering an injection of 1 mg per kilo active ingredient, given four times each day.

9. The method of claim 3 wherein the $PGB_1$ oligomer is selected from the group consisting of $PGB_1$-Dimer, -$PGB_2$-Trimer, 16,16'-diMethyl-PGB Dimer and 16,16'-diMethyl-PGB Trimer.

* * * * *